United States Patent [19]
Bengtsson et al.

[11] Patent Number: 5,240,957
[45] Date of Patent: Aug. 31, 1993

[54] OXYSALICYLAMIDO DERIVATIVES

[75] Inventors: Karl S. Bengtsson; Thomas Hogberg, both of Jarna; Lars G. Johansson, Södertälje; Tomas DePaulis, Rönninge; Hans E. P. Ström, Järna; Marianne E. Widman, Täby; Sven O. Ögren, Nykvarn, all of Sweden

[73] Assignee: Astra Lakemedel Akteibolag, Sodertalje, Sweden

[21] Appl. No.: 607,746

[22] Filed: Oct. 29, 1990

Related U.S. Application Data

[63] Continuation of Ser. No. 313,339, Feb. 21, 1989, abandoned, which is a continuation of Ser. No. 52,181, May 4, 1987, abandoned, which is a continuation-in-part of Ser. No. 687,471, Dec. 28, 1984, abandoned.

[30] Foreign Application Priority Data

Jan. 31, 1984 [SE] Sweden ................. 8400478

[51] Int. Cl.⁵ ............... A61K 31/40; A61K 31/36; C07D 207/09; C07D 405/02
[52] U.S. Cl. ................. 514/428; 514/422; 548/526; 548/567
[58] Field of Search ............. 548/567; 514/428, 422

[56] References Cited

U.S. PATENT DOCUMENTS

| | | | |
|---|---|---|---|
| 3,342,826 | 9/1967 | Miller et al. | 548/567 X |
| 3,591,634 | 7/1971 | Thominet | 548/567 X |
| 3,594,417 | 7/1971 | Thominet | 548/567 X |
| 4,029,673 | 6/1977 | Bulteau et al. | 548/567 |
| 4,232,037 | 11/1980 | Florvall et al. | 562/474 X |
| 4,816,471 | 3/1989 | Thominet et al. | 548/567 X |

FOREIGN PATENT DOCUMENTS

| | | |
|---|---|---|
| 0054936 | 8/1982 | European Pat. Off. . |
| 0060235 | 9/1982 | European Pat. Off. . |
| 0067615 | 12/1982 | European Pat. Off. . |
| 0117384 | 9/1984 | European Pat. Off. . |
| 639369 | 11/1983 | Switzerland . |
| 2126585A | 3/1984 | United Kingdom ........ 548/567 |

OTHER PUBLICATIONS

Florvall, et al., Journal of Med. Chem., (1982), vol. 25, pp. 1280-1286.
Philbin, et al., C.A., 51, col. 12890i-12891d, (1957).
Gilman, et al., C.A., 38, col. 3 & 77(7-9) (1944).

*Primary Examiner*—Joseph Paul Brust
*Attorney, Agent, or Firm*—White & Case

[57] ABSTRACT

Novel therapeutically active compounds of the formula

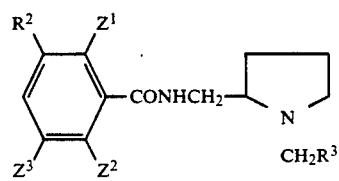

wherein
$Z^i$, being $Z^1$, $Z^2$ or $Z^3$, is the same or different and selected among OH, $OR^1$, $NH_2$, $NR_2^4$, $NHR^4$, SH, $SR^4$ and $OR^4$ wherein $R^1$ is a formyl group, an acyl group, an alkoxycarbonyl group or a mono- or dialkylcarbamoyl group and $R^4$ is a lower alkyl group,
$R^2$ is a hydrogen, a halogen, a lower alkyl or a lower trifluoroalkyl group,
$R^3$ is a hydrogen atom, a lower alkyl group, an alkenyl group, an alkynyl group or a phenyl group, which phenyl group could optionally be substituted by one or more of fluoro, chloro, bromo, trifluoromethyl, methyl, ethyl, methoxy or ethoxy in the ortho, meta or para positions, or optionally substituted by methylenedioxy, provided that at least one of $Z^1$, $Z^2$ and $Z^3$ is a group $OR^4$ and further provided that when $Z^2$ is OH or $NH_2$, $Z^1$ is $NR_2^4$, $NHR^4$, SH, $SR^4$ or $OR^4$ or a physiologically acceptable salt or optical isomer thereof, intermediates and methods for their preparation, pharmaceutical preparations containing the compounds and methods for their therapeutical use.

14 Claims, No Drawings

OXYSALICYLAMIDO DERIVATIVES

This application is a continuation of Ser. No. 313,339, filed Feb. 21, 1989, now abandoned, which is a continuation of U.S. Ser. No. 052,181, filed May 4, 1987, now abandoned, which is a continuation-in-art of Ser. No. 687,471, filed Dec. 28, 1984, now abandoned.

FIELD OF THE INVENTION

The present invention relates to novel, pharmacologically active derivatives of oxy-substituted salicylamides, intermediates and processes for their preparation, pharmaceutical compositions containing the oxysalicylamido derivatives and to methods of their pharmacological use.

The object of the invention is to provide a substituted benzamide neuroleptic useful for the blockade of dopamine receptors in the brain. Such substances will be useful in the treatment of emesis, anxiety states, psychomatic diseases and psychotic states, such as schizophrenia and depression, alcoholic related diseases, confusional states and sleep disturbances in the elderly.

PRIOR ART

Remoxipride (U.S. Pat. No. 4,232,037) with the formula

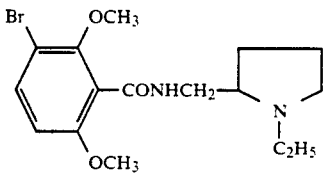

is a recently developed antipsychotic agent. This compound is claimed to be a potent antagonist of the apomorphine syndrome in the rat.

In European Patent Application No. 60235 benzamido derivatives claimed to be potent inhibitors of the apomorphine syndrome in the rat, are disclosed, among these the compound of the formula

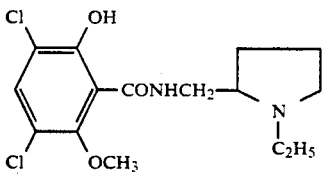

The compounds of U.S. Pat. No. 4,232,037 and EP 60235 have less potent antidopaminergic effects than the compounds of the present invention.

DISCLOSURE OF THE INVENTION

The present invention relates to compounds of the formula

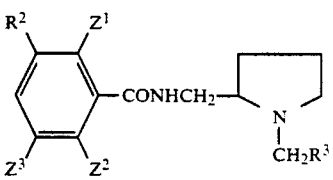     I wherein $Z^i$, being $Z^1$, $Z^2$ or $Z^3$, is the same or different and selected among OH, $OR^1$, $NH_2$, $NR_2^4$, $NHR^4$, SH, $SR^4$ and $OR^4$ wherein $R^1$ is a formyl group, an acyl group, an alkoxycarbonyl group or a mono- or dialkylcarbamoyl group and $R^4$ is a lower alkyl group, $R^2$ is a hydrogen, a halogen, a lower alkyl or a lower trifluoroalkyl group, $R^3$ is a hydrogen atom, a lower alkyl group, an alkenyl group, an alkynyl group or a phenyl group, which phenyl group could optionally be substituted by one or more of fluoro, chloro, bromo, trifluoromethyl, methyl, ethyl, methoxy or ethoxy in the ortho, meta or para positions, or optionally substituted by methylenedioxy, provided that at least one of $Z^1$, $Z^2$ and $Z^3$ is a group $OR^4$ and further provided that when $Z^2$ is OH or $NH_2$, $Z^1$ is $NR_2^4$, $NHR^4$, SH, $SR^4$ or $OR^4$ or a physiologically acceptable salt or optical isomer thereof.

It has been found that such compounds have valuable therapeutical properties, particularly they have more potent antidopaminergic effects than the prior art compounds discussed above and they also exhibit a larger separation to drug induced extrapyramidal side effects.

The invention thus provides compounds, and physiologically acceptable salts thereof, which compounds are useful in therapeutic treatment of emesis, anxiety states, psychosomatic diseases such as gastric and duodenal ulcer, and psychotic states such as schizophrenia and depression, alcoholic related diseases, confusional sates and sleep disturbances in the elderly.

Halogen atoms in formula I comprise chloride, bromine, fluorine and iodine atoms.

Lower alkyl groups in formula I are straight or branched alkyl groups with 1 to 4 carbon atoms, such as methyl, ethyl, n-propyl, i-propyl, n-butyl, s-butyl, i-butyl and t-butyl.

Lower trifluoroalkyl group in formula I is a group $F_3C-(CH_2)_n-$ wherein n is 0, 1 or 2.

Alkenyl groups in formula I are straight or branched hydrocarbon chains with 2 to 3 carbon atoms and a double bond, such as vinyl, allyl or isopropenyl.

Alkynyl groups in formula I are hydrocarbon chains with 2 to 3 carbon atoms with a triple bond, that is $-C\equiv CH_3$, $-CH_2-C\equiv CH_3$ and $-C\equiv CCH_3$.

Acyl groups in formula I are alkyl—CO— where the alkyl moiety is a straight or branched hydrocarbon chain with 1 to 17 carbon atoms, preferably 1-15 carbon atoms.

Alkoxycarbonyl groups in formula I are alkyl—O—CO wherein the alkyl moiety is a hydrocarbon chain with 1-17 C as defined above, preferably 1-15 C.

Monoalkylcarbamoyl groups in formula I are groups alkyl—NH—CO— wherein the alkyl moiety is a hydrocarbon chain with 1-17 C as defined above, preferably 1-15 C.

Dialkylcarbamoyl groups in formula I are groups

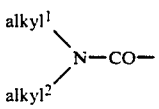

wherein the alkyl[1] and alkyl[2] can be the same or different and each is a hydrocarbon chain with 1-17 C as defined above, preferably 1-15 C.

Phenyl substituted with methylenedioxy in formula I is the group

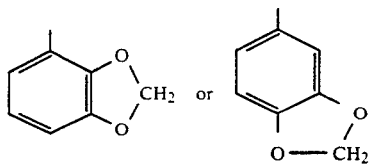 or 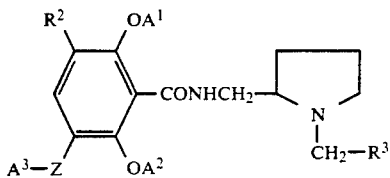

Compounds of the formula I A below are falling within the general scope of the invention:

IA

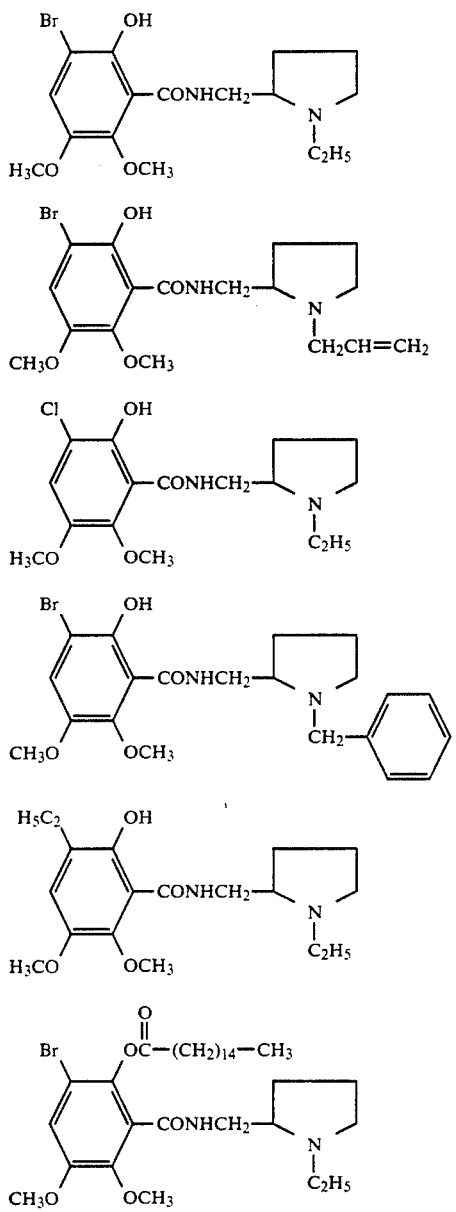

wherein $A^3$ is a hydrogen atom, or a lower alkyl group, $R^2$ is a hydrogen atom, a halogen atom, a lower alkyl group or a lower trifluoroalkyl group, Z is a moiety selected among oxygen, sulphur, nitrogen and alkyl-substituted nitrogen, $A^1$ is a hydrogen atom, a lower alkyl group, a formyl group, an acyl group, an alkoxycarbonyl group or a mono- or di-alkylcarbamoyl group, $A^2$ is a methyl or an ethyl group, $R^3$ is a hydrogen atom, a lower alkyl group, an alkenyl group, an alkynyl group or a phenyl group, which phenyl group could optionally be substituted by one or more of fluoro, chloro, bromo, trifluoromethyl, methyl, ethyl, methoxy or ethoxy in the ortho, meta or para positions, or optionally substituted by methylenedioxy.

or a physiologically acceptable salt or optical isomer thereof.

Preferred groups of compounds of the invention is obtained when in formula I a) $Z^1$, $Z^2$ and $Z^3$ is OH, OMe, OEt, O-acyl, $NH_2$, NHMe, NHEt, $NMe_2$ and $NEt_2$ with one or more of $Z^1$, $Z^2$ and $Z^3$ being OMe or OEt, $R^2$ is Cl, Br, I, Me, Et, Pr, $R^3$ is hydrogen, methyl, ethyl, vinyl, ethynyl or substituted phenyl group, or b) $Z^1$, $Z^2$ and $Z^3$ is OH, OMe, OEt, O-acyl and $NH_2$ with one or more of $Z^i$ being OMe or OEt;

$R^2$ is Cl, Br, Et, Pr $R^3$ is as in a), or c) $Z^1$, $Z^2$ and $Z^3$ is OH, OMe and O-acyl with one or more of $Z^i$ being OMe, $R^2$ is Cl, Br, Et, Pr $R^3$ is methyl, ethyl, vinyl or substituted phenyl, or d) $Z^1$ is OH or O-acyl $Z^2$ and $Z^3$ is OMe $R^2$ is Cl, Br, Et, Pr $R^3$ is methyl or vinyl and the configuration of the pyrrolidine ring being S (sinister) or phenyl or para-halogen substituted phenyl and the configuration of the pyrrolidine ring being R (rectus).

Compounds particularly preferred are

The new compounds of this invention may be used therapeutically as the racemic mixtures of (+)- and (−)-forms, which are obtained by synthesis. They may also be resolved into the corresponding enantiomers which, likewise, may be used in therapy. The (+)- and (−)-forms may also be obtained by the reaction of the corresponding enantiomeric 2-aminomethylpyrrolidine derivative with the benzoic acid moiety.

The compounds of this invention may be administered in the form of free bases or their salts with non-toxic acids. Some typical examples of these salts are the hydrobromide, hydrochloride, phosphate, sulphate, sulphonate, sulphamate, citrate, lactate, maleate, tartrate and acetate.

Pharmaceutical preparations

In clinical practice the compounds of the present invention will normally be administered orally, rectally or by injection in the form of pharmaceutical preparations comprising the active ingredient either as a free base or as a pharmaceutically acceptable non-toxic, acid addition salt, e.g. the hydrobromide, hydrochloride, phosphate, sulphate, sulphonate, sulphamate, citrate lactate, maleate, tartrate, acetate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept.

The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparations intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives or gelatine, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine, talcum, titanium dioxide, and the like.

Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped closed capsules) consisting of gelatine and for example, glycerol or similar closed capsules, the active substance may be admixed with a vegetable oil. Hard gelatin capsules may contain granulations of the active substance in combination with solid, powder carriers such as lactose, saccharose, sorbitol, mannitol, starches (e.g. potato starch, corn starch or amylopectin), cellulose derivatives or gelatin.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2 to about 20% by wight of the active substance herein described, the balance being sugar and a mixture of ethanol water, glycerol, and propyleneglycol. Optionally such liquid preparations may contain colouring agents, flavoring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5 to about 10% by weight. These solutions may also contain stabilizing agents and/or buffering agents and may conveniently be provided in various dosage unit ampoules.

Compounds of the formula I wherein $R^1$ is an acyl group, an alkoxycarbonyl group or a mono- or dialkylcarbamoyl group may advantageously be used in pharmaceutical preparations intended for intramuscular administration in order to obtain a sustained release effect, that is a depot effect.

Suitable daily doses for oral administration of the compounds of this invention are 1–50 mg, preferably 5–20 mg.

Methods of preparation

The compounds of the invention may be obtained by one of the following methods.

A. The compounds of the formula

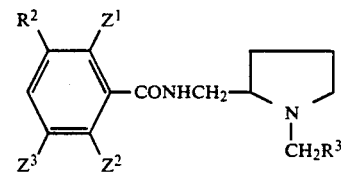

wherein $Z^i$, being $Z^1$, $Z^2$ or $Z^3$, is the same or different and selected among OH, $OR^1$, $NH_2$, $NR_2^4$, SH, $SR^4$ and $OR^4$ wherein $R^1$ is a formyl group, an acyl group, an alkoxycarbonyl group or a mono- or dialkylcarbamoyl group and $R^4$ is a lower alkyl group, $R^2$ is a hydrogen, a halogen, a lower alkyl or a lower trifluoroalkyl group, $R^3$ is a hydrogen atom, a lower alkyl group, an alkenyl group, an alkynyl group or a phenyl group, which phenyl group could optionally be substituted by one or more of fluoro, chloro, bromo, trifluoromethyl, methyl, ethyl, methoxy or ethoxy in the ortho, meta or para positions, or optionally substituted by methylenedioxy, provided that at least one of $Z^1$, $Z^2$ and $Z^3$ is a group $OR^4$ and further provided that when $Z^2$ is OH or $NH_2$, $Z^1$ is $NR_2^4$, $NHR^4$, SH, $SR^4$ or $OR^4$, can be obtained by reaction of a compound of the formula

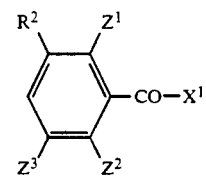

wherein $Z^1$, $Z^2$, $Z^3$ and $R^2$ have the above given definitions and —CO—$X^1$ is a reactive group capable of reacting with an amino group under formation of an amide moiety, with a compound of the formula

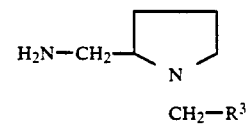

wherein $R^3$ has the above given definition, or a reactive derivative thereof.

The reaction is carried out in a suitable solvent, such as diethyl ether, THF, dichloromethane, chloroform or toluene between $-20°$ C. and the boiling point of the reaction mixture. The resulting amine can be isolated as a salt recovered e.g. by filtration. Alternatively, the amine obtained can be converted to the free base using conventional techniques, such as the addition of aqueous ammonia or a sodium hydroxide solution, and extraction with an organic solvent.

$X^1$ in the acylating group —CO—$X^1$ may be a halogen group, such as chlorine or bromine, a mixed anhydride with inorganic acids or their esters, e.g. phenylphosphate, a thio group, an organic residue, or a hydroxy group in combination with a coupling agent or reactive amine derivative.

The organic residue comprises groups which can form reactive acid derivatives. These can be aliphatic esters, e.g. methyl, ethyl, cyanomethyl or methoxymethyl esters, N-hydroxyimide esters or substituted or unsubstituted aromatic esters; acyl nitrile; acyl azide; symmetrical anhydrides; mixed anhydrides; or azolides, e.g. triazolide, tetrazolide or imidazolide.

According to the invention the following compounds can be used as reactive derivatives of the cyclic amine above:

Reaction products of the amine with phosphorus chloride, phosphorus oxychloride, dialkyl, diaryl or o-phenylenechlorophosphites or alkyl or aryldichlorophosphites, or an isothiocyanate or isocyanate of the amine. The mentioned reactive derivatives can be reacted with the acid in situ or after previous isolation.

It is also possible to react the free acid and the free amine in the presence of a condensating agent, e.g. silicon tetrachloride, diphosphoruspentoide, a phosphine or hexamethylphosphorous triamide plus a carbon tetrahalide, diphenyl phosphite, N-ethoxycarbonyl-2-ethoxy-1,2-dihydroquinoline, titanium tetrachloride, or carbodiimides such as diccylohexylcarbodiimide, N,N'-carbonyldimidizole, N,N'-thionyldiimidazole and diethyldiazodicarboxylate.

B. The compounds of the formula I, wherein $R^2$ and $R^3$ are as defined in A and $Z^1$, $Z^2$ and $Z^3$ are the same or different and selected among OH, $OR^1$ and $OR^4$ can be obtained by N-substitution of a compound of the formula

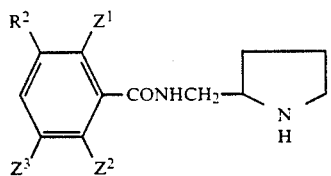

wherein $R^2$, $Z^1$, $Z^2$ and $Z^3$ have the definition given above, with a compound of the formula

$$R^3-CH_2-X^2$$

wherein $R^3$ has the definition given in A and $X^2$ is a leaving group, such as chlorine, bromine, sulphate, phosphate, bensenesulphonate or toluenesulphonate.

The reaction can be effected by treating the reactants at 0° C.-100° C. in a suitable solvent, e.g. acetone, alcohols, dimethylformamide (DMF), dimethylsulphoxide (DMSO) in the presence of a base, for example NaOH or $K_2CO_3$.

C. The compounds of the formula I with the definition as in A with the exception that one of $Z^1$, $Z^2$ and $Z^3$ is $NH_2$ and the others OH, $OR^1$, $OR^4$ or $SR^4$, can be obtained by reduction of a compound of the formula

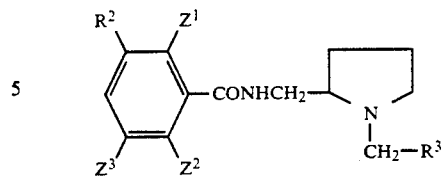

wherein $R^2$ and $R^3$ have the definition given in A and one of $Z^1$, $Z^2$ and $Z^3$ is $NO_2$ and the others are OH, $OR^1$, $OR^4$ or $SR^4$.

The reduction can be performed by catalytic hydrogenation ($R^2 \neq$ halogen) or by treatment with $FeSO_4 \times 7H_2O$ in ammonia.

D. The compounds of the formula I wherein $Z^1$, $Z^2$ or $Z^3$ is the same or different and selected among OH, and $OR^4$, $NH_2$, $NHR^4$, SH and $SR^4$ and $R^2$ and $R^3$ are as defined in A can be obtained by reduction of a compound of the formula

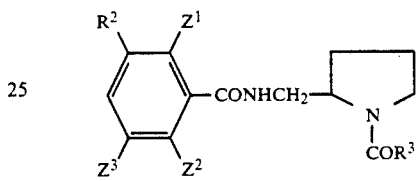

wherein $R^2$, $R^3$, $Z^1$, $Z^2$ and $Z^3$ have the definition given above.

Suitable reducing agents working on the less sterically hindered amide group are a) $LiAlH_4$ and alkoxy complexes thereof; b) $NaBH_4$ with addition of transition metal salts, or $AlCl_3$ or $BF_3$ or $POCl_3$ or carboxylic acids such as $CH_3COOH$ and $CF_3COOH$; c) $B_2H_6$.

The reaction is preferably effected in alkyl ethers, such as diethylether, dimethoxyethane, diglyme, THF, dioxane, at temperatures from 0° C. to reflux temperatures of the reaction mixtures.

E. The compounds of the formula I with the definition as in A with the exception that one or two of $Z^1$, $Z^2$ and $Z^3$ is a hydroxy group, can be obtained by deprotection of a compound of the formula

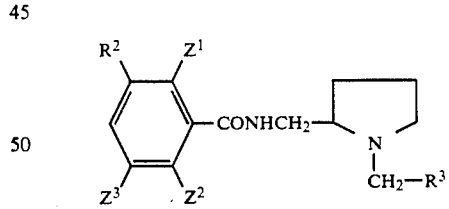

wherein $R^2$, $R^3$, $Z^1$, $Z^2$ and $Z^3$ have the above definition with the exception that $Z^1$, $Z^2$ and $Z^3$ are suitably protected phenol groups corresponding to the hydroxyl groups in the product.

Suitable standard phenol protective groups can be groups such as trimethylsilyl, t-butyldimethylsilyl, tetrahydropyranyl, benzyl, methoxyethoxymethyl, methoxymethyl, methylthiomethyl, aliphatic or aromatic esters, carbonates or cyclic acetals, ketals or esters when $Z^2 = Z^3 =$ OH in the product. The protective groups can be removed by standard procedures (T. W. Greene, in "Protective Groups in Organic Synthesis", Wiley, New York, 1981, p. 87–113).

A special form of protective group is represented by $Z^1$ or $Z^2$ being alkoxy.

Thus, the compounds of the formula I with the definition as in A, with the exception that $Z^1$ or $Z^2$ is hydroxy and the remaining $Z^i$ being OH, $OR^4$, $NH_2$, $NR_2^4$, $NHR^4$, or $SR^4$, can be obtained by dealkylation of a compound of the formula

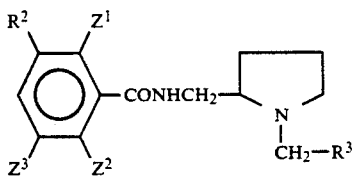

wherein $R^2$, $R^3$, $Z^1$, $Z^2$ and $Z^3$ have the above definition with the exception that $Z^1$ or $Z^2$ being $OR^4$, resulting in the corresponding hydroxy compound in the reaction.

Suitable reagents are Brönsted acids (HBr, HI), Lewis acids ($AlCl_3$, $AlBr_3$, $AlI_3$, $BBr_3$, $BCl_3$, 9-bromo-9-borabicyclo[3.3.0]nonane, $NaBH_4/I_2$), nucleophilic reagents (sodium ethanethiolate, sodium phenylmethaneselenolate) and others (iodtrimethylsilane).

The reaction with Brönsted acids is performed at elevated temperatures preferably with a co-solvent like acetic acid or in the presence of a phase-transfer catalyst. The reaction with Lewis acids can be performed in refluxing benzene or carbon disulfide (aluminum halides) and halogenated solvents like dichloromethane at $-75°$ C. to $25°$ C. (boron halides). Elevated temperature in dimethylformamide is suitable for nucleophilic reagents.

F. The compounds of the formula I with the definition as in A with the exception that $R^2$ is Br or Cl can be obtained by reaction of a compound of the formula

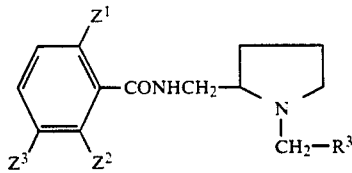

wherein $R^3$, $Z^1$, $Z^2$ and $Z^3$ have the above given definition with a halogenating reagent such as halogen, a sulphurylhalogenide (preferably sulphurylchloride) or a halogen-dioxane complex.

Chlorination is effected by treating the starting compound with chlorine with or without Lewis acid catalysis or with sulphurylchloride, HOCl, N-chloromaides in the presence of acid catalyst in suitable solvent, e.g. chloroform, nitrobenzene.

Bromination is carried out with $Br_2$ with or without Lewis acid catalysis or bromination in acetic acid in the presence of a base e.g. sodium acetate or by using bromine-dioxane complex. Other reagents can be used among them HOBr and N-bromoamides especially N-bromosuccinimide with acid catalysts.

G. The compounds of the formula I with the definition as in A with the exception that $Z^1$ and/or $Z^2$ is $OR^4$, $NR_2^4$ or $SR^4$ can be obtained by reaction of a compound of the formula

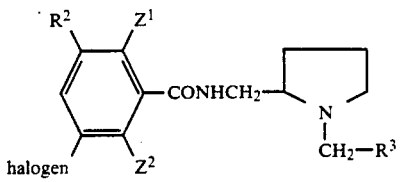

wherein $R^2$, $Z^1$, $Z^2$ and $R^3$ have the above given definition and halogen is e.g. Cl, Br or I, with potassium hydroxide or sodium hydroxide in aqueous media, such as water in DMSO.

The reaction may be performed in water at $100°$ C. in the presence of copper bronze or copper sulphate.

H. The compounds of the formula I with the definition as in A with the exception that $R^2$ is a hydrogen atom can be obtained by catalytic hydrogenation of a compound of the formula

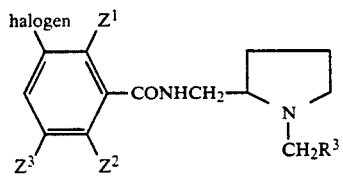

wherein $R^3$, $Z^1$, $Z^2$ and $Z^3$ have the above given definition, and halogen is e.g. Cl, Br or I.

The reaction is effected in a suitable solvent, e.g. methanol, ethanol.

I. The compounds of the formula I with the definition that at least one $Z^i$ is $OR^1$ and the remaining $Z^i$ are (is) $OR^4$, $NR_2^4$ or $SR^4$ and the definition of $R^2$ and $R^3$ as in A, can be obtained by reaction of a compound of the formula

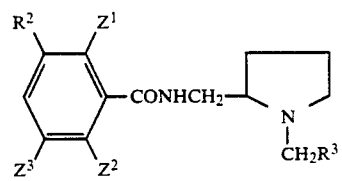

wherein $R^2$ and $R^3$ have the above definition and $Z^i$ is defined as above with the exception that the $Z^i$ which is/are $OR^1$ in the end product is OH in the staring material, with a compound of the formula $R^1$-$X^3$ wherein $R^1$ has the above given definition and $X^3$ is a suitable leaving group such as halogen, (Cl, Br), acyloxy, azide or azolide without solvent or in a suitable solvent such as benzene or chloroform possibly with acid catalysis (e.g. $CF_3COOH$, $H_2SO_4$) or by using a tertiary amine as solvent and/or catalyst.

In the case of $R^1$ being monoalkylcarbamoyl the reaction can also be performed with an isocyanate.

Intermediates

The compounds of the formula

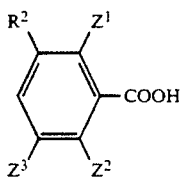

wherein $Z^i$, being $Z^1$, $Z^2$ or $Z^3$, is the same or different and selected among OH, $OR^1$, $NH_2$, $NR_2^4$, $NHR^4$, SH, $SR^4$ and $OR^4$ wherein $R^1$ is a formyl group, an acyl group, an alkoxycarbonyl group or a mono- or dialkylcarbamoyl group and $R^4$ is a lower alkyl group, $R^2$ is a hydrogen, a halogen, a lower alkyl or a lower trifluoroalkyl group, provided that at least one of $Z^1$, $Z^2$ and $Z^3$ is a group $OR^4$ and further provided that when $Z^2$ is OH or $NH_2$, $Z^1$ is $NR_2^4$, $NHR_2$, SH, $SR^4$ or $OR^4$ or $OR^4$ are valuable intermediates for the preparation of the compounds of this invention by the process A.

The compounds of the formula

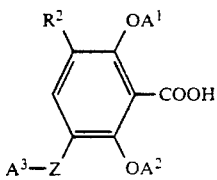

wherein $A^3$ is a hydrogen atom, or a lower alkyl group, $R^2$ is a hydrogen atom, a halogen atom, a lower alkyl group or a lower trifluoroalkyl group, Z is a moiety selected among oxygen, sulphur, nitrogen and alkyl-substituted nitrogen, $A^1$ is a hydrogen atom, a lower alkyl group, a formyl group, an acyl group, an alkoxycarbonyl group or a mono- or di-alkylcarbamoyl group, $A^2$ is a methyl or an ethyl group, are a subgroup within the group of compounds of the formula I.

Compounds of the formula I wherein one, two or three of $Z^1$, $Z^2$ and $Z^3$ is a suitably protected phenol group are valuable intermediates for the preparation of deprotected compounds of the invention according to the process E.

The compounds of the formula

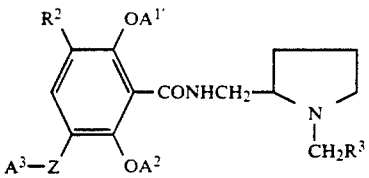

wherein $A^3$ is a hydrogen atom, or a lower alkyl group, $R^2$ is a hydrogen atom, a halogen atom, a lower alkyl group or a lower trifluoroalkyl group, Z is a moiety selected among oxygen, sulphur, nitrogen and alkyl-substituted nitrogen, $A^{1'}$ is a lower alkyl group, $A^2$ is a methyl or an ethyl group, $R^3$ is a hydrogen atom, a lower alkyl group, an alkenyl group, an alkynyl group or a phenyl group, which phenyl group could optionally be substituted by one or more of fluoro, chloro, bromo, trifluoromethyl, methyl, ethyl, methoxy or ethoxy in the ortho, meta or para positions, or optionally substituted by methylenedioxy, are a subgroup within the group of compounds of the formula I, useful as intermediates for the preparation of dealkylated compounds of this invention.

The intermediates are prepared by the method described in A.

Intermediate of the formula

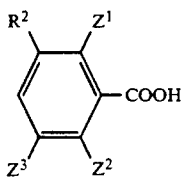

wherein $R^2$, $Z^1$, $Z^2$ and $Z^3$ are as defined above, may be prepared by i) treating a compound of the formula

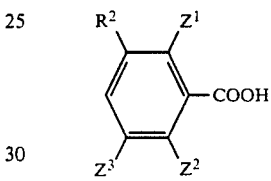

wherein $R^2$ is as defined above and $Z^1$, $Z^2$ and $Z^3$ are $OR^4$, wherein $R^4$ is as defined above, with a Lewis acid such as boron tribromide, boron trichloride or aluminum chloride or hydrobromic acid, ii) treating a compound of the formula

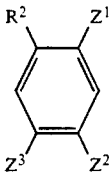

wherein $R^2$ is as defined previously with the exception of Br and I; $Z^1$, $Z^2$ and $Z^3$ being alkoxy, dialkylamino or alkylthio; alternatively $Z^1$, $Z^2$ and $Z^3$ can be a suitably protected derivative like methoxymethyl ether, tetrahydropyranyl ether, t-butoxycarbonylamine or t-butylcarbonylamin which is deprotected after the reaction, with alkyl- or aryllithium followed by reaction with carbon dioxide and acidification.

iii) treating a compound of the formula

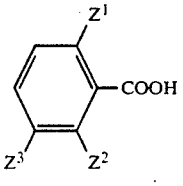

wherein $Z^1$, $Z^2$ and $Z^3$ are as defined previously, with halogen, a sulfurylhalogenide (preferably $SO_2Cl_2$) or a halogen-dioxane complex gives compounds with $R^2$ being halogen.

WORKING EXAMPLES

Example 1

(S)-(−)-N-[(1-ethyl-2-pyrrolidinyl)methyl]-3-bromo-2,5,6-trimethoxybenzamide Method A.

A solution of 3-bromo-2,5,6-trimethoxybenzoic acid (4.5 g, 0.015 mol) in 60 ml toluene was treated with thionyl chloride (4.5 g, 0.038 mol) at 65° C. for 1 h. The solvent was evaporated and the residue dissolved in 20 ml CHCl$_3$. A solution of (S)-(−)-N-[(2-aminomethyl-1-ethyl-pyrrolidine in 40 ml CHCl$_3$ was added. The temperature rose to 45° C. After 0.5 h the solvent was removed and the residue was neutralized with 100 ml 1-M NaOH. Extraction with 3×100 ml ether, drying and evaporation gave 5.8 g of title compound. Crystallization from diisopropylether gave 4.8 g (79%). M.p. 106°–107° C. NRM: One aromatic singlet at 7.07 ppm and three methoxy singlets at 3.86, 3.85 and 3.84 ppm. Carbon-13 signals at 164.6(7), 149.9(5), 147.6(2), 145.9(6), 128.6(1), 117.0(4) and 111.1(3) ppm, respectively.

Anal. ($C_{17}H_{25}BrN_2O_4$) %C: calc. 50.88, found 50.84; %H: calcd. 6.28, found 6.27; %N: calcd. 6.98, found 6.96.

Example 2

(S)-(−)-N-[(1-ethyl-2-pyrrolidinyl)methyl]-3-chloro-2,5,6-trimethoxybenzamide Method A.

3-chloro-2,5,6-trimethoxybenzoic acid 2,5,6-trimethoxybenzoic acid 5.0 g (0.024 mol) was suspended in 75 ml of CHCl$_3$ and cooled to 0° C. 1.9 ml (0.024 mol) of SO$_2$Cl$_2$ was added under N$_2$-atm. The reaction was stirred for 2 hr and allowed to slowly attain room temperature. The reaction mixture was diluted 100 ml CHCl$_3$ and washed with 200 ml H$_2$O. The aqueous layer was washed with 50 ml CHCl$_3$ and the combined organic layer was dried (Na$_2$SO$_4$) and the solvent was evaporated. Gave 5.5 g (95%) of 3-chloro-2,5,6-trimethoxybenzoic acid (oil). Mw: 246.7.

(S)-(−)-N-[(1-ethyl-2-pyrrolidinyl)methyl]-3-chloro-2,5,6-trimethoxybenzamide A solution of 3-chloro-2,5,6-trimethoxybenzoic acid 5.5 g (0.023 mol), DMF and SOCl$_2$ in toluene was stirred at 50° C. under N$_2$-atm. until gas evolution steps. The solvent was evaporated and the residue was dissolved in 100 ml CHCl$_3$ and evaporated again. The residue was dissolved in 75 ml CHCl$_3$ and mixture with a solution of (S)-(−)-2-aminoethyl-1-ethylpyrrolidine in 10 ml CHCl$_3$. The mixture was stirred at room temperature for 3 hours and then extracted with 2×100 ml 1M HCl. The combined aqueous layer was alkalified with 45% NaOH (aq) and then extracted with 2×150 ml CH$_2$Cl$_2$. The combined organic layer was dried (Na$_2$SO$_4$) and the solvent was evaporated. Gave 4.8 g (60%) crystallizing residue. Recrylstallization from 50 ml iPr$_2$O gave 2.1 g of title compound, m.p. 118°–120° C. (26%).

Example 3

(S)-(−)-N-[(1-ethyl-2-pyrrolidinyl)methyl]-2,3,6-trimethoxybenzamide Method A.

2,3,6-Trimethoxybenzoic acid (4.2 g 0.020 mol) was treated with thionyl chloride (7.1 g, 0.060 mol) in toluene (150 ml) at 65° C. for 1 h. The solvent was removed in vacuo and the residue was dissolved in 50 ml chloroform. A solution of (S)-(−)-N-ethyl-2-aminomethylpyrrolidine (3.8 g, 0.030 mol) in 50 ml chloroform was added and stirred at 40° C. for 30 min. Addition of sodium hydroxide (20 ml, 2-N), separation and evaporation of the organic layer gave 4.5 g of title compound Features of the nuclear magnetic resonance spectrum are given below.
$^1$H NMR (CDCl$_3$)δppm, 6.87 (d,1H), 6.58 (d,1H,J=9.1 Hz), 3.88 (s,3H), 3.82 (s,3H), 3.78 (s,3H).
$^{13}$C NMR (CDCl$_3$)δppm, 165.6, 150.2, 147.0, 146.9, 114.3, 113.4, 106.5.

Example 4

(S)-(−)-N-[(1-ethyl-2-pyrrolidinyl)methyl]-3-ethyl-2,5,6-trimethoxybenzamide Method A.

3-Ethyl-2,5,6-trimethoxybenzoic acid (2.0 g, 0.0083 mol) was treated with thionyl chloride (1.2 g, 0.010 mol) in 20 ml toluene, containing 3 drops of dimethylformamide as a catalyst, at 50° C. for 1.5 h. The solvent was removed. The residue, consisting of crude 3-ethyl-2,5,6-trimethoxybenzoyl chloride, was dissolved in 20 ml chloroform and mixed with a solution of (S)-(−)-1-ethyl-2-aminomethylpyrrolidine (1.3 g, 0.010 mol) in 20 ml chloroform. After 16 h the reaction mixture was extracted with 2×50 ml 1-N HCl. The aqueous layer was made alkaline with 30% NaOH. Extraction with 2×75 ml chloroform, drying (Na$_2$SO$_4$) and evaporation of the solvent gave 2.0 g. Yield 71%. M.p. 85°–87° C. from diisopropylether. $[\alpha]_D^{20} = -71°$ (c=0.74, acetone). $^{13}$C-NMR (CDCl$_3$)δ166.0 (CONH), 149.1 (C-2), 148.2 (C-6), 144.3 (C-5), 133.0 (C-3), 127.2 (C-1), 113.8 (C-4) (aromatic signals only) ppm.

Example 5

(S)-(−)-N-[(1-Ethyl-2-pyrrolidinyl)methyl]-3-propyl-2,5,6-trimethoxybenzamide (Method A)

3-Propyl-2,5,6-trimethoxybenzoic acid (23 g, 0.09 mol) was treated with thionyl chloride and (2S)-(−)-1-ethyl-2-aminomethylpyrrolidine as described in example 4. Yield 10.6 g (32%). M.p. 68°–70° C. (i-Pr$_2$O). $^1$H-NMR (CDCl$_3$): δ6.73 (s,1H), 6.40 (b,1H), 3.85 (Sx2,6H), 3.76 (s,3H), 0.9–3.8 (m,21H)ppm.

Example 6

(R)-(+)-N-[(1-Benzyl-2-pyrrolidinyl)methyl]-3-bromo-2,5,6-trimethoxybenzamide (Method A) 3-Bromo-2,5,6-trimethoxybenzoyl chloride (8 mol) was reacted with (2R)-1-benzyl-2-aminomethylpyrrolidine (6.5 mmol) in 15 ml dichloromethane in analogy with example 1. Purification by flash chromatography on SiO$_2$ with i-Pr$_2$O/MeOH/NH$_3$ 100:10:1 as eluent gave 1.17 g (39%). M.p. 112°–114° C. $[\alpha]_D^{22} = +57°$ (c=0.52, acetone). $^1$H-NMR (CDCl$_3$): Three methoxy singlets at 3.85, 3.84 and 3.83 ppm. $^{13}$C-NMR (CDCl$_3$): δ164.7 (CONH), 149.9, 147.7, 146.1, 139.3, 128.9, 128.7, 128.3, 127.0, 117.3, 111.1 (aromatic) ppm. Mass spectrum (EI, 70 eV): m/z 464/462 (M, 0.14%/0.11%), 160 (100%), 91 (52%).

Example 7

(S)-(+)-N-[(1-Ethyl-2-pyrrolidinyl)methyl]-2-amino-3-bromo-5,6-dimethoxybenzamide (Method A)

To a solution of 2-amino-3-bromo-5,6-dimethoxybenzoic acid (0.96 g, 3 mmol) and triethylamine (0.58 ml, 4.2 mmol) in 15 ml tetrahydrofuran//dichloromethane (1:1) was added ethyl chloroformate (0.32 ml, 3.4 mmol) at −20° C. After stirring for 45 min. at −20° C. a solution of (2S)-(−)-1-ethyl-2-aminomethylpyrrolidine in 10 ml dichloromethane was added at −20° C. After stirring for 3 h at room temperature the mixture was washed with water and extracted with 0.5M HCl. The aqueous phase was made alkaline and extracted twice with dichloromethane. Drying (Na$_2$SO$_4$) and evaporation gave 0.45 g crude material which was purified by chromatography on a C$_{18}$ reversed phase column with H$_2$O/MeOH/NH$_3$ 40:60:0.3 as eluent to give 0.25 g (22%) pure product as an oil.

Anal. (C$_{16}$H$_{24}$BrN$_3$O$_3$): Calcd: C, 49.75; H, 6.26; N, 10.88. Found: C, 49.90; H, 6.31; N, 10.69.

$^1$H-NMR (CDCl$_3$):δ1.11 (t,CH$_3$), 1.7–3.9 (multiplets, 11 H), 3.80 and 3.82 (two s, (OMe)$_2$), 5.80 (b, NH$_2$), 7.14 (s,4-H), 7.9 (b, NH)ppm. $^{13}$C-NMR (CDCl$_3$):δ167.0 (CONH), 148.1, 143.7, 140.9, 120.3, 113.0, 104.9 (aromatic) ppm.

Example 8

(S)-(−)-N-[(1-ethyl-2-pyrrolidinyl)methyl]-3-bromo-5-hydroxy-2,6-dimethoxybenzamide Method A.

3,5-Dibromo-2,6-dimethoxybenzoic acid (10.0 g, 0.036 mol) was dissolved in 200 ml 10% sodium hydroxide. 1.0 g of copper bronze powder was added and the mixture was heated at 100° C. for 6 h. After cooling the mixture was neutralized with concentrated hydrochloric acid and extracted with 2×200 ml methylene chloride. Drying and evaporation of the solvent gave 3.5 g of brown resine consisting of 3-bromo-5-hydroxy-2,6-dimethoxybenzoic acid.

The residue was treated with thionyl chloride (3.5 g, 0.03 mol) in 50 ml toluene at 65° C. for 1 h. The solvent was removed in vacuo and the residue was dissolved in 30 ml chloroform. A solution of (S)-(−)-N-1-ethyl-2-aminomethylpyrrolidine in 15 ml chloroform was added and the mixture was stirred for 1 h at 35° C. Water and 20 ml 2-N NaOH was added. The product was extracted with chloroform and subjected to column chromatography (Si-gel, Merck Lichrosorb in CH$_2$Cl$_2$—C$_2$H$_5$OH—NH$_3$, 90:9:1). Gave 0.35 g of title compound as an oil.

Mass spectrum: Molecular peak 386/388 corresponding to C$_{16}$H$_{23}$BrN$_2$O$_4$.

NMR: (CDCl$_3$) proton: δppm 7.56 (b, 5-OH), 7.03 (s, H$_4$), 6.83 (b, NH), 3.80 (s, CH$_3$O), 3.77 (s, CH$_3$O), 1.7–3.8 (m, 11H), 1.11 (t, CH$_3$). Carbon-13: δppm 165.4 CONH, 147.2 C$_5$OH, 146.6 C$_2$-OMe, 144.4 C$_6$-OMe, 127.0 C$_1$-CONH, 121.2 C$_4$-H, 111.3 C$_3$-Br.

Example 9

(S)-(−)-N-[(1-ethyl-2-pyrrolidinyl)methyl]-3-bromo-2-hydroxy 5,6-dimethoxybenzamide and (S)-(−)-3-Bromo-N-[(1-ethyl-2-pyrrolidinyl)methyl]-6-hydroxy-2,5-dimethoxybenzamide Method E.

a) Compound (S)-(−)-N-[(1-ethyl-2-pyrrolidinyl)methyl]-3-bromo-2,5,6-trimethoxybenzamide (8.1 g, 0.020 mol) was dissolved in 100 ml CH$_2$Cl$_2$. 3-M HCl-ether (7.3 ml, 0.022 mol) was added at room temperature followed by a solution of boron tribromide (5.5 g, 0.022 mol) in 40 ml CH$_2$Cl$_2$. After 1 h at 25° C. 2-M ammonia (50 ml) was added, and the organic layer was separated, dried and evaporated. The residue (6.1 g) shows two peaks in GC with retention times 8.5 and 6.8 min, respectively, and two spots on TLC (silica in methanol-diisopropylether, 1:4) in the ratio 2:1. The major product was isolated by column chromatography to give 3.0 g of first title product. The hydrochloride was crystallized from 15 ml acetone-ether, M.p. 135°–137° C.

Anal. (C$_{16}$H$_{24}$BrClN$_2$O$_4$): %C: calcd 45.35, found 45.22; %H: calcd 5.71, found 5.67 %N: calcd 6.61, found 6.56; %Br: calcd 18.86, found 18.75; %Cl: calcd 8.36, found 8.47.

$^1$H-NMR: (CDCl$_3$,δppm) 7.28 (s, 1H), 3.93 (s, 3H), 3.84 (s, 3H), 3.70 (dd, 1H), 3.30 (m, 2H), 2.84 (dq, 1H), 2.6 (m, 1H), 2.20 (m, 2H), 1.4–1.8 (m, 4H), 1.13 (t, 3H).

$^{13}$H-NMR: aromatic region 169.2, 153.5, 147.9, 144.6, 121.9, 109.0, 105.5

From the collected fractions above which contained the minor compound 0.92 g of second title product was obtained, M.p. 97°–99° C. from hexaneethanol (20:1).

$^1$H-NMR: (CDCl$_3$): δ8.9 (b, NH), 7.06 (s, H-4), 3.86 (s, OCH$_3$), 3.84 (s, OCH$_3$), 1.6–3.9 (m, 12H), 1.13 (t, CH$_3$) ppm. $^{13}$C-NMR (CDCl$_3$): δ169.1 (CONH), 153.4 (C-2), 148.8 (C-6), 146.7 (C-5), 118.2 (C-4), 108.9 (C-1), 103.8 (C-3), (aromatic) ppm.

$[\alpha]_D^{20} = -53°$ (C=1.52, acetone).

b) From an anhydrous stock solution of (S)-(−)-N-[(1-ethyl-2-pyrrolidinyl)methyl]-3-bromo-5,6-dimethoxy-2-trimethylsilyloxybenzamide was withdrawn 0.5 mmol and treated with water at room temperature which caused rapid formation of the first title compound which had identical NMR and GC retention time as the compound described in a).

Example 10

(S)-(−)-N-[(1-ethyl-2-pyrrolidinyl)methyl]-3-chloro-2-hydroxy 5,6-dimethoxybenzamide and (S)-(−)-3-Chloro-N-[(1-ethyl-2-pyrrolidinyl)methyl]-6-hydroxy-2,5-dimethoxybenzamide Method E.

To a solution of 2.0 g (S)-(−)-N-[(1-ethyl-2-pyrrolidinyl)methyl]-3-chloro-2,5,6-trimethoxyhydroxybenzamide (0.0056 mol) and 1.9 ml 3M HCl-ether (0.0056 mol) in 20 ml CH$_2$Cl$_2$, was a solution of 1.4 g BBr$_3$ in 10 ml CH$_2$Cl$_2$ added, over a period of 1 hour. After 1 hour at room temperature was the reaction mixture extracted with concentrated ammonia. The alkalified aqueous layer was extracted with 2×100 ml CH$_2$Cl$_2$. The organic layer was dried (Na$_2$ SO$_4$) and evaporated. Gave a residue 1.3 g. TLC (silica in iPr$_2$O:-MeOH:NH$_3$ 89:10:1) showed two spots Rf 0.45 and Rf 0.30, respectively. 0.9 g of the mixture was separated by column chromatography and gave 0.4 g of the first title compound. The mesylate was crystallized from acetone, M.p. 165°–166° C.

Anal. (C$_{16}$H$_{23}$ClN$_2$O$_4$): %C: calcd 46.52, found 46.53; %H; calcd 6.20, found 6.14; %Cl: calcd 8.08, found 7.89; %N: calcd 6.38, found 6.30; %O: calcd 25.52, found 25.39: %S: calcd 7.31, found 7.38.

From the collected fractions above, which contained the minor compound, was prepared 0.10 g of the second title compound as an oil. $[\alpha]_D^{20} = -62°$ (c=0.18, acetone).

$^1$H-NMR (CDCl$_3$):δ8.9 (b, NH), 6.92 (s, H-4), 3.86 (s, (OCH$_3$)$_2$), 1.6–3.8 (m, 11H), 1.13 (t, CH$_3$) ppm.

$^{13}$C-NMR (CDCl$_3$):δ169.4 (CONH), 153.1 (C-6), 148.0 (C-2), 146.6 (C-5), 115.9 (C-4), 115.7 (C-3), 108.8 (C-1) (aromatic) ppm.

Example 11

(S)-(−)-N-[(1-ethyl-2-pyrrolidinyl)methyl]-3-ethyl-2-hydroxy-5,6-dimethoxybenzamide and (S)-(−)-N-[(1-Ethyl-2-pyrrolidinyl)methyl]-3-ethyl-6-hydroxy-2,5-dimethoxybenzamide Method E.

A solution of (S)-(−)-N-[(1-ethyl-2-pyrrolidinyl)methyl]-3-ethyl-2,5,6-trimethoxyhydroxybenzamide (0.80 g, 0.002 mol) in 25 ml CH$_2$Cl$_2$ was treated with 3-N HCl-ether (1 ml, 0.003 mol) followed by the addition of a solution of boron tribromide (0.6 g, 0.0023 mol) in 10 ml $CH_2Cl_2$ at ambient temperature. Work up and chromatography in accordance with example 9 gave 0.4 g (54)) of the first title compound as an oil. Proton NMR: (CDCl$_3$) δppm: 9.2 (b, NH), 6.92 (s, H$_4$), 3.90 (s, CH$_3$O), 3.84 (s, CH$_3$O), 1.7–3.8 (m, 13H), 1.17 (t, CH$_3$), 1.13 (t, CH$_3$). Carbon-13 NMR: (CDCl$_3$)δppm: 170.2 CONH, 154.7 C$_2$-OH, 146.3 C$_6$-OCH$_3$, 143.8 C$_5$-OCH$_3$, 128.3 C$_3$-C$_2$H$_5$, 119.0 C$_4$-H, 107.5 C$_1$-CONH. GC: Retention time 6.6 min. at 260° C. on 10 m SE 54. The minor isomer has RT 7.8 m.

The mesylate was prepared from ether by mixing one equivalent of methanesulfonic acid in acetone and recrystallizing from acetone. M.p. 153°–155° C. (acetone). Yield 0.32 g (38%).

Analysis ($C_{19}H_{32}N_2O_7S$): %C: calcd 52.76, found 52.69; %H: calcd 7.46, found 7.33; %N: calcd 6.48, found 6.44; %O: calcd 25.89, found 25.76; %S: calcd 7.41, found 7.27.

From the collected fractions above containing the minor isomer was prepared 0.3 g of the second title compound as the methanesulfonate. M.p. 137°–138° C. from acetone. $[\alpha]_D^{20}$ (base) = −48° (c = 1.0, acetone).

$^1$H-NMR (CDCl$_3$):δ8.9 (b, NH), 6.79 (s, H-4), 3.87 (s, OCH$_3$), 3.71 (s, OCH$_3$), 1.6–3.9 (m, 13H), 1.23 (t, CH$_3$), 1.13 (t, CH$_3$)ppm. $^{13}$C-NMR (CDCl$_3$):δ170.2 (CONH), 151.9 (C-6), 149.8 (C-2), 146.1 (C-5), 125.5 (C-3), 115.8 (C-4), 108.0 (C-1) (aromatic) ppm.

Example 12

(S)-(−)-5,6-Dimethoxy-N-[(1-ethyl-2-pyrrolidinyl)-methyl]-2-hydroxy-3-propylbenzamide (Method E).

A solution of 10.0 g (0.27 mol) of (S)-(−)-N-[(1-ethyl-2-pyrrolidinyl)methyl]-3-propyl-2,5,6-trimethoxybenzamide was treated with 16 ml (0.027 mol) of 1.6M HCl-ether in 250 ml of methylene chloride. A solution of 6.8 g (0.027 mol) of boron tribromide in 50 ml methylene chloride was slowly added at 10° C. The reaction mixture was stirred for 2 h at 20° C. 100 ml of 2M NH$_3$ was added. Extraction with 2×300 ml of CH$_2$Cl$_2$, drying (Na$_2$SO$_4$) and evaporation of the solvent gave 9.2 g of two components in a 4:1 ratio. The residue was dissolved in 300 ml of ether and shaken with 2×50 ml of 1N NaOH which exclusively removed the minor component from the ether layer. Drying and evaporation of the solvent gave 6.0 g of the title compound as an oil. GC 5.5 min at 250° C. (SE-54). Yield 63%.

$^{13}$C-NMR (CDCl$_3$)δ170.2 (CONH), 154.9 (C-2), 146.3 (C-6), 143.6 (C-5), 126.7 (C-3), 119.9 (C-4), 107.5 (C-1), 62.2 (OCH$_3$), 62.1 (OCH$_3$), 61.2 (C$^1$-2), 57.2, 53.4, 47.7, 40.5, 32.0, 28.4, 22.6, 14.0, 13.9 (9 carbons) ppm.

The oil was dissolved in 75 ml acetone. A hot solution of 2.6 g of L(+)-tartaric acid in 95 ml 98% (aq) acetone was added which gave 4.5 g of the tartrate salt. M.p. 84°–85° C.

Example 13

(S)-(−)-2,5-Dimethoxy-N-[(1-ethyl-2-pyrrolidinyl)-methyl]-6-hydroxy-3-propylbenzamide Method E.

The combined alkaline aqueous layer of example 12 was washed with 50 ml ether and neutralized with ammonium chloride to pH 8.5. Extraction with 2×50 ml ether gave 1.3 g of pure minor isomer as an oil. GC (SE-54, 250° C.) 6.0 min.

$^1$H-NMR (CDCl$_3$):δ8.5 (b, NH), 6.77 (s, H-4), 3.86 (s, OCH$_3$), 3.71 (s, OCH$_3$), 1.6–3.9 (m, 15H), 1.13 (t, 3H), 0.98 (t, 3H) ppm. $^{13}$C-NMR (CDCl$_3$):δ170.1 (CONH), 151.8 (C-6), 149.9 (C-2), 145.8 (C-5), 123.9 (C-3), 115.8 (C-4), 107.9 (C-1) (aromatic) ppm.

Example 14

(S)-(−)-N-[(1-Allyl-2-pyrrolidinyl)methyl]-3-bromo-2-hydroxy-5,6-dimethoxybenzamide and (S)-(−)-N-[(1-Allyl-2-pyrrolidinyl)methyl]-3-bromo-6-hydroxy-2,5-dimethoxybenzamide (Method E)

By the same method as described in example 9, (S)-(−)-N-[(1-Allyl-2-pyrrolidinyl)methyl]-3-bromo-2,5,6-trimethoxyhydroxybenzamide prepared in example 21 was transformed into the first title compound. Yield 48% of colorless oil. $[\alpha]_D^{20}$ = −62° (c = 1.8, acetone).

$^1$H-NMR (CDCl$_3$):δ9.05 (b, NH), 7.27 (s, H-4), 5.91 (m, vinyl-H), 5.19 (dd, 1H), 5.12 (d, 1H), 3.92 (s, OCH$_3$), 1.6–3.8 (m, 11H) ppm. $^{13}$C-NMR (CDCl$_3$):δ169.3 (CONH), 153.6 (C-2), 148.0 (C-6), 144.6 (C-5), 135.9 (CH-4), 122.0 (vinyl-CH), 117.0 (vinyl-CH$_2$), 109.1 (C-1), 105.6 (C-3), 61.5 (CH-2'), 61.4 (OCH$_3$-5), 57.2 (OCH$_3$-6), 56.9 (NHCH$_2$), 54.2 (NCH$_2$), 40.6 (CH$_2$-5'), 28.4 (CH$_2$-3'), 22.8 (CH$_2$-4') ppm.

From the fractions containing the minor component was isolated 0.06 g of the second title compound as an oil. $[\alpha]_D^{20}$ = −51° (c = 0.18, acetone). $^1$H-NMR (CDCl$_3$):δ8.9 (b, NH), 7.07 (s, H-4), 5.90 (m, 1H), 5.30 (dd, 1H, J = 22 Hz, 1.5 Hz), 5.16 (d, 1H, J = 16 Hz), 3.87 (s, OCH$_3$), 3.84 (s, OCH$_3$), 1.6–3.8 (m, 11H) ppm.

Example 15

(R)-(+)-N-[(1-Benzyl-2-pyrrolidinyl)methyl]-3-bromo-2-hydroxy-5,6-dimethoxybenzamide and (R)-(+)-N-[(1-Benzyl-2-pyrrolidinyl)methyl]-3-bromo-6-hydroxy-2,5-dimethoxybenzamide (Method E).

(R)-(+)-N-[(1-Benzyl-2-pyrrolidinyl)methyl]-3-bromo-2,5,6-trimethoxybenzamide (950 mg, 2.05 mmol) was dissolved in 30 ml dichloromethane and cooled with ice. Solutions of 4M HCl in ether (0.5 ml, 2 mmol) followed by 3.2 ml 0.65M boron tribromide in dichloromethane (2.1 mmol) were added. After stirring for 1 h 30 ml 0.7M NH$_3$ were added, the mixture extracted with dichloromethane. The solvent was evaporated, the residue dissolved in Et$_2$O, washed with brine, dried (MgSO$_4$) and evaporated to give 923 mg (100%) of two isomeric phenols. GC (SE 30, capillary column, 270° C.): retention times 10.1 min and 12.4 min (ratio 3:7). The phenols were separated by flash chromatography on SiO$_2$ with Et$_2$O/MeOH/NH$_3$ 100:3:0.3 to give 495 mg (54%) of the first title compound as an oil.

$[\alpha]_D^{22}$ = +94° (c = 0.52, acetone). $^1$H-NMR (CDCl$_3$):δ7.25 (s, overlapping with Ph, 4-H), 3.81 and 3.75 (two s, (OMe)$_2$). Mass spectrum (EI, 70 ev): m/z 449/447 (M-H, 0.57/0.61%), 261/259 (ArCO, 1.3/1.3%), 160 (100%), 91 (51%).

From the fractions containing the minor component was isolated 229 mg (25%) of the second title compound as an oil. $[\alpha]_D^{22}$ = +81° (c = 1.1, acetone). $^1$H-NMR (CDCl$_3$):δ7.12 (s, 4-H), 3.79 and 3.84 (two s, (OMe)$_2$).

Mass spectrum (EI, 70 eV): m/z 449/447 (M-H, 0.31/0.33%), 261/259 (ArCO, 0.86/0.91%), 160 (100%), 91 (54%).

Example 16

(S)-(−)-N-[(1-Ethyl-2-pyrrolidinyl)methyl]-5,6-dimethoxy-2-hydroxybenzamide hydrochloride (Method H)

A solution of (S)-(−)-N-[(1-Ethyl-2-pyrrolidinyl)methyl]-2-hydroxy-5,6-dimethoxybenzamide HCl (0.20 g, 0.47 mmol) in 10 ml of 95% ethanol was hydrogenated for 2.5 h at ambient pressure and temperature with 10 mg of palladium on charcoal as the catalyst. Filtration and evaporation of the solvent gave 0.18 g of the title products as an oil. Its chromatographic and spectroscopic properties (TLC, GC, NMR) were identical of those of the minor product obtained from the boron tribromide demethylation of (S)-(−)-N-[(1-ethyl-2-pyrrolidinyl)methyl]-2,5,6-trimethoxybenzamide.

Gas chromatography (GC): Retention time at 230° C. on 25 m SE-52 in 2.50 min (72% of that of its isomer).

NMR: proton (CDCl$_3$)δppm 8.4 (b,NH), 7.02 (d,J=9.15 Hz,H$_4$), 6.70 (d,H$_3$), 3.93 (s,CH$_3$O), 3.83 (s,CH$_3$O), 1.7–3.8 (m,11H), 1.13 (t,CH$_3$CH$_2$).

NMR: carbon-13 (CDCl$_3$)δppm: 169.8 CONH, 156.9 C$_2$-OH, 148.3 C$_6$-OMe, 144.4 C$_5$-OMe, 118.9 C$_4$-H, 113.1 C$_3$-H, 108.3 C$_1$-CONH.

Example 17

(S)-(−)-N-[(1-ethyl-2-pyrrolidinyl)methyl]-5-hydroxy-2,6-dimethoxybenzamide (Method G)

(S)-(−)-3-Bromo-N-[(1-ethyl-2-pyrrolidinyl)methyl]-2,6-dimethoxybenzamide ×HCl×H$_2$O (1.0 g, 0.0026 mol) was dissolved in 25 ml dimethylsulphoxide. A suspension of crushed potassium hydroxide (1.0 g, 0.018 mol) in 5 ml water was added and the mixture was heated at reflux for 2 h. After cooling 200 ml of water was added and the reaction mixture was neutralized and extracted with chloroform. Drying and evaporation of the solvent gave a residue containing a mixture of several products including the starting material. Separation on silica column with CH$_2$Cl$_2$-C$_2$H$_5$OH-NH$_3$ (90:9:1) gave 0.05 g of the title compound as a oil.

NMR: (CDCl$_3$)δppm 9.0 (b,NH), 6.88 (d,J=9.15 Hz,H$_4$), 6.29 (d,H$_5$), 3.95 (s,CH$_3$O), 3.93 (s,CH$_3$O), 1.7–3.8 (m,11H), 1.14 (t,CH$_3$).

The chromatographic and spectroscopic properties (TLC, GC, NMR, MS) were identical of those of the product obtained by catalytic hydrogenation of (S)-(−)-3-bromo-N-[(1-ethyl-2-pyrrolidinyl)methyl]-5-hydroxy-2,6-dimethoxybenzamide.

Example 18

(S)-(−)-5-Amino-3-bromo-N-[(1-ethyl-2-pyrrolidinyl)methyl]-2-hydroxy-6-methoxybenzamide (Method C)

Iron(II) sulphate heptahydrate (11 g, 0.04 mol) was dissolved in 25 ml water and added to a solution of (S)-(−)-3-bromo-N-[(1-ethyl-2-pyrrolidinyl)methyl]-2-hydroxy-5-nitro-6-methoxybenzamide (2.0 g, 0.005 mol) in 50 ml methanol. 30 ml concentrated ammonia (25%) was added and the mixture was stirred at 60° C. for 1 h. Filtration and washing the precipitation with methanol-water (1:1) was followed by neutralization with ammonium chloride to pH 8. Extraction with 4×75 ml ether, drying (Na$_2$SO$_4$) and evaporation of the solvent gave 1.0 g of residue which crystallized upon standing. The dihydrochloride monohydrate was precipitated from HCl-ether and recrystallized from ethanol. M.p. 102°–105° C. (dec.)

Carbon-13 NMR (CDCl$_3$)δppm: 169.2 CONH, 152.1 C$_2$-OH, 145.2 C$_6$-OCH$_3$, 132.1 C$_5$-NH$_2$, 124.5 C$_4$-H, 109.2 C$_1$-CONH, 107.3 C$_3$-Br.

Analysis (C$_{15}$H$_{26}$BrCl$_2$N$_3$O$_4$): %C: calcd 38.90, found 39.04; %H: cacld 5.66, found 5.32; %Br: calcd 17.25, found 17.17; %Cl: calcd 15.31, found 15.18; %N: calcd 9.07, found 9.05.

Example 19

(S)-(−)-5-Amino-3-bromo-N-[(1-ethyl-2-pyrrolidinyl)methyl]-2,6-dimethoxybenzamide (Method C)

(S)-(−)-3-Bromo-N-[(1-ethyl-2-pyrrolidinyl)methyl]-5-nitro-2,6-dimethoxybenzamide (2.1 g, 0.005 mol) was dissolved in a mixture of 50 ml methanol and 30 ml 14-N ammonia. A solution of iron(II) sulphate heptahydrate in 25 ml of water was added and the mixture was stirred at 60° C. for 45 min. The inorganic salts were filtered off, washed with 50 ml aqueous methanol (50%), and the combined filtrate was extracted with 2×100 ml ether. The combined extract was neutralized with conc. HCl and shaken with 3×75 ml 1-N HCl. The combined aqueous layer was treated with 30% NaOH to pH 10 and extracted with 3×100 ml ether. Drying and evaporation of the solvent gave 1.84 g of crude product as an oil. It was dissolved in 50 ml CH$_2$Cl$_2$ and 2 ml of 3-N HCl-ether was added. Evaporation of the solvent and dissolving the residue in 15 ml 2-propanol gave 1.8 g of the dihydrochloride monohydrate of the title compound upon addition of 45 ml ethyl acetate, M.p. 110° C. (dec.). Yield 75%.

NMR: 6.9 (s,H$_4$), 6.5 (b,NH), 4.0 (b,NH$_2$), 3.8 s(CH$_3$O+CH$_3$O), 1.7–3.8 (m,11H), 1.1 (t,CH$_3$).

Analysis (C$_{16}$H$_{28}$BrCl$_2$N$_3$O$_4$): %C: calcd 40.27, found 40.76; %H: cacld 5.91, found 5.86; %Br: calcd 16.74, found 16.22; %Cl: calcd 14.86, found 14.01; %N: calcd 8.81, found 8.36.

Example 20

(S)-(−)-N-[(1-ethyl-2-pyrrolidinyl)methyl]-5-amino-2-hydroxy-6-methoxybenzamide (Method C)

By the same method as described in Example 19 the following compound was prepared:

(S)-(−)-N-[(1-ethyl-2-pyrrolidinyl)methyl]-5-amino-2-hydroxy-6-methoxybenzamide.

M.p. of the dihydrochloride: 102°–105° C. from ethanol.

Example 21

(S)-(−)-N-[(1-Allyl-2-pyrrolidinyl)methyl]-3-bromo-2,5,6-trimethoxybenzamide (Method B)

3-Bromo-2,5,6-trimethoxybenzamide chloride (1.48 g, 4.8 mmol) was reacted with (S)-(−)-1-trityl-2-aminomethylpyrrolidine (1.51 g, 4.4 mmol) in 10 ml dichloromethane at room temperature for 1 h. The solvent was evaporated and the residue was treated with 10 ml ethanol and 0.1 ml conc. HCl during 1 h. After evaporation the residue was partitioned between 0.5M HCl and Et$_2$O. The aqueous phase was made alkaline, extracted with dichloromethane, dried (Na$_2$SO$_4$) and evaporated to give 1.30 g (79%) (S)-(+)-3-bromo-N-(2-pyrrolidinylmethyl)-2,5,6-trimethoxybenzamide. An analytical sample of the hydrochloride was prepared. M.p. 181°–182° C. (EtOH/acetone/Et$_2$O).

To a mixture of (S)-(+)-3-bromo-N-2-pyrrolidinylmethyl)-2,5,6-trimethoxybenzamide (0.82 g, 0.0022 mol) and potassium carbonate (0.40 g, 0.003 mol) in 10 ml of dimethylformamide, allylbromide (0.40 g, 0.0033 mol) in 4 ml DMF was added dropwise at 20° C. After 1 hr 150 ml of water was added and the product was extracted with ether. The combined organic layer was shaken with 3×50 ml of 1N HCl and the combined aqueous layer was made alkaline by addition of 20 ml of 10N NaOH. Extraction with methylene chloride (2×75 ml) gave 0.8 g of the desired benzamide. Crystallization from 12 ml of diisopropylether gave 0.33 g. M.p.

118°–122° C. $[\alpha]_D^{20} = -85°$ (c=0.44, acetone). $^1$H-NMR (CDCl$_3$):δ7.07 (s,1H), 6.34 (b, 1H), 5.85 (m, 1H), 5.12 (dd, 2H), 3.86 (s, 3H), 3.84 (sx2, 6H), 3.76 (m, 1H), 3.35 (m, 2H), 3.04 (m, 1H, 2.88 (m, 1H), 2.67 (b, 1H), 2.22 (m, 1H), 1.60–1.98 (m, 3H), ppm. $^{13}$C-NMR (CDCl$_3$):δ164.6 (CONH), 149.9 (C-2), 147.6 (C-5), 1458.8 (C-6), 135.9 (C-4, 128.6 (C-1, 117.0 (allyl), 116.9 (allyl), 111.1 (C-3) ppm.

Example 22

(S)-(−)-N-[(1-Ethyl-2-pyrrolidinyl)methyl]-3-bromo-2-hydroxy-5,6-dimethoxybenzamide (Method F).

(S)-(−)-N-[(1-Ethyl-2-pyrrolidinyl)methyl]-2-hydroxy-5,6-dimethoxybenzamide (140 mg, 0.45 mmol) was dissolved in 5 ml dioxane. After addition of 0.1 g K$_2$CO$_3$ a solution of 30 µl Br$_2$ in 2 ml dioxane was added. After stirring for 2 h the mixture was partitioned between 2M NH$_3$ and Et$_2$O. Drying (MgSO$_4$) and evaporation of the organic layer gave 165 mg (95) of the title compound having identical NMR and GC retention time as the compound prepared in Example 9.

Example 23

(S)-N-[(1-Ethyl-2-pyrrolidinyl)methyl]-3-bromo-2-hexadecanoyl-5,6-dimethoxybenzamide (Method I)

To a solution of (S)-N-[(1-ethyl-2-pyrrolidinyl)methyl]-3-bromo-2-hydroxy-5,6-dimethoxybenzamide mesylate (0.48 g, 1 mmol) in 10 ml of trifluoroacetic acid was added palmitoyl chloride (0.55 ml, 2 mmol). The reaction mixture was stirred at ambient temperature over molecular sieves for 20 h. After evaporation of the solvent in vacuo ether was added to the residue and filtered. The filtrate was washed several times with a saturated KHCO$_3$ solution and dried (MgSO$_4$). After evaporation of the solvent in vacuo the resulting oil crystallized on cooling. Yield 0.42 g (67%). M.p. 46°–48° C. R$_f$ value is 0.21 for title compound and 0.32 for starting compound (SiO$_2$, TLC-plates, 20% MeOH in i-Pr$_2$O as eluent).

Mass spectrum (EI, 70 eV) m/z 624/626 (M+).

Example 24

(S)-(−)-N-[(1-Ethyl-2-pyrrolidinyl)methyl]-3,6-dibenzyloxy-2-methoxybenzamide (Method A)

A solution of 3,6-dibenzyloxy-2-methoxybenzamide acid (120 mg, 0.33 mmol), thionyl chloride (120 mg, 1 mmol) and two drops of dimethylformamide as catalyst in 5 ml toluene was stirred at 60° C. for 1.5 h. The solvent was evaporated and the residue dissolved in CH$_2$Cl$_2$ and evaporated again. This residue was dissolved in 8 ml CH$_2$Cl$_2$ and a solution of (S)-(−)-1-ethyl-2-aminomethylpyrrolidine (65 mg, 0.5 mmol) in 2 ml CH$_2$Cl$_2$ was added. After stirring overnight at room temperature the solvent was evaporated and the residue partitioned between 2M HCl and ether. The aqueous phase was made alkaline, extracted with CH$_2$Cl$_2$, dried (Na$_2$SO$_4$) and evaporated to give a crude product. Purification by chromatography on SiO$_2$ with iPr$_2$O/hexane/MeOH/NH$_3$ 69:20:10:1 as eluent gave 145 mg (93%) pure title compound. M.p. 121°–123° C. $[\alpha]_D^{22} = -42°$ (c=2.8, acetone). $^1$H NMR (CDCl$_3$)δ7.39 and 7.38 )two s, CH$_2$Ph), 6.89 and 6.59 (AB, 4-H and 5-H), 5.06 and 5.03 (two s, CH$_2$Ph), 3.95 (s, OMe) ppm. Mass spectrum (EI, 70 eV): m/z 474 (M, 0.13%), 347 (ArCO, 0.33%), 98 (100%), 91 (12%)

Example 25

(S)-(−)-N-[(1-Ethyl-2-pyrrolidinyl)methyl]-3,6-dihydroxy-2-methoxybenzamide (Method E)

A mixture of (S)-(−)-N-[(1-ethyl-2-pyrrolidinyl)methyl]-3,6-dibenzyloxy-2-methoxybenzamide (130 mg, 0.27 mmol), 5% Pd/C (50 mg), 0.5 ml 4 M HCl in ether and 5 ml ethanol was shaken in a hydrogen atmosphere for 1 h. Filtration and evaporation of the solvent gave 90 mg pure title compound as an oily hydrochloride.

$^1$H NMR (CDCl$_3$/CD$_3$OD):δ7.13 and 6.67 (AB, 4-H and 5-H), 3.99 (s, OMe) ppm.

Mass spectrum (EI, 70 eV): m/z 294 (M, 0.64%), 167 (ArCO, 1.4%), 98 (100%).

Example 26

(S)-(−)-N-[(1-Ethyl-2-pyrrolidinyl)methyl]-3-bromo-2,5-dihydroxy-6-methoxybenzamide (Method F)

To a mixture of (S)-(−)-N-[(1-ethyl-2-pyrrolidinyl)methyl]-3,6-dihydroxy-2-methoxybenzamide hydrochloride (90 mg, 0.27 mmol), 0.5 ml dioxane and 0.1 ml acetic acid was added a solution of 18 µl bromine (0.35 mmol) in 0.5 ml dioxane. After stirring at room temperature for 1 h the solvent was evaporated.

$^1$NMR (CDCl$_3$) showed complete removal of the aromatic AB system: δppm 7.40 (s, 4-H), 4.05 (s, OMe) ppm.

Mass spectrum (EI, 70 eV): m/z 374/372 (M, 0.19%/0.18%), 247/245 (ArCO, 0.40%/0.40%), 98 (100%.

Example 27

By any of the methods described in the preceding examples the following compounds could be prepared:

(S)-(−)-N-[(1-ethyl-2-pyrrolidinyl)methyl]-2-hydroxy-5,6-dimethoxy-3-methylbenzamide, (S)-(−)-N-[(1-ethyl-2-pyrrolidinyl)methyl]-5-bromo-2,3-dihydroxy-6-methoxybenzamide, (S)-(−)-N-[(1-ethyl-2-pyrrolidinyl)methyl]-3-ethyl-2,5-dihydroxy-6-methoxybenzamide, (S)-(−)-N-[(1-ethyl-2-pyrrolidinyl)methyl]-5-amino-3-ethyl-2-hydroxy-6-methoxybenzamide, (S)-(−)-N-[(1-ethyl-2-pyrrolidinyl)methyl]-3-bromo-2-hydroxy-6-methoxybenzamide,

Example 28

The following examples illustrate the preparation of pharmaceutical compositions of the invention. The wording "active substance" denotes a compound according to the present invention or a salt thereof.

Formulation A. Soft gelatin capsules 500 g of active substance were mixed with 500 g of corn oil, whereupon the mixture was filled in soft gelatin capsules, each capsule containing 100 mg of the mixture (i.e. 50 mg of active substance).

Formulation B. Soft gelatin capsules 500 g of active substance were mixed with 750 g of pea nut oil, whereupon the mixture was filled in soft gelatin capsules, each capsule containing 125 mg of the mixture (i.e. 50 mg of active substance).

Formulation C. Tablets 50 kg of active substance were mixed with 20 kg of silicic acid of the trademark Aerosil. 45 kg of potato starch and 50 kg of lactose were mixed therewith and the mixture was moistened with a starch paste prepared from 5 kg of potato starch and distilled water, whereupon the mixture was granulated through a sieve. The granulate was dried and sieved, whereupon 2 kg of magnesium stearate was mixed into it. Finally the mixture was pressed into tablets each weighing 172 mg.

Formulation D. Effervescing tablets 100 g of active substance, 140 g of finely divided citric acid, 100 g of finely divided sodium hydrogen carbonate, 3.5 g of magnesium stearate and flavouring agents (q.s.) were mixed and the mixture was pressed into tablets each containing 100 mg of active substance.

Formulation E. Sustained release tablet 200 g of active substance were melted together with 50 g of stearic acid and 50 g of carnauba wax. The mixture thus obtained was cooled and ground to a particle size of at most 1 mm in diameter. The mixture thus obtained was mixed with 5 g of magnesium stearate and pressed into tablets each weighing 305 mg. Each tablet thus contains 200 mg of active substance.

Formulation F. Injection solution

| Active substance | 3.000 mg |
| Sodium pyrosulfite | 0.500 mg |
| Disodium edetate | 0.100 mg |
| Sodium chloride | 8.500 mg |
| Sterile water for injection | ad 1.00 ml |

Formulation G. Hard gelatine capsules 10 g of active substance was mixed with 400 g of lactose and finally 2 g of magnesium stearate was added. The mixture was then filled in hard gelatine capsules, each capsule containing 206 mg of the mixture (i.e. 5 mg of active substance).

Formulation H. Tablets 50 g of active substance was mixed with 1500 g of lactose, 200 g of microcrystalline cellulose and 10 g magnesium stearate. Tablets of 5 mg active substance with a core weight of 176 mg were finally comprotted.

Formulation I. Depot preparation

| (S)-N-[(1-ethyl-2-pyrrolidinyl)-methyl]-3-bromo-2-hexadecanoyl-5,6-dimethoxybenzamide | 200 mg |
| Peanut oil | ad 1 ml |

PHARMACOLOGY

Introduction

A number of studies suggest that the antipsychotic action of neuroleptic drugs is in some way related to the decrease in catecholamine transmission in the brain caused by these drugs and more specifically due to central dopamine (DA) receptor blockage in cortical and subcortical brain regions. Most compounds with an antipsychotic action affect several DA systems in the brain. There is evidence that the antipsychotic action may be linked to blockade of DA receptors in the subcortical and cortical limbic structures (J. Pharm. Pharmacol. 25, 346, 1973; Lancet, 1027, 1976) while the wellknown extrapyramidal side effects produced by neuroleptic drugs are due to blockage of DA receptors in the nigroneostriatal DA system (Intern. J. Neurol. 6, 27-45, 1967).

A. In vivo tests

There are presently several techniques available to study DA receptor blockage in the brain in vivo. One method is based on the ability of antipsychotic drugs to block the behavioral effects induced by the DA agonist apomorphine in the rat. Several studies indicate an excellent correlation between the in vivo DA receptor blockage as measured in the apomorphine test and therapeutic efficacy of different antipsychotic drugs. Apomorphine produces in rats and other species a characteristic syndrome consisting of repetitive movements (stereotypies) and hyperactivity which appear to be due to activation of postsynaptic DA receptors in the brain (J. Pharm. Pharmacol. 19, 627, 1967; J. Neurol. transm. 40, 97-113, 1977). The stereotypies (chewing, licking, biting) appear mainly to be induced via activation of DA receptors linked to the nigro neostriatal DA system (J. Psychiat. Res., 11, 1, 1974) whereas the increased locomotion (hyperactivity) mainly appears to be due to activation of DA receptors in subcortical mesolimbic structures (nucleus olfactorium, nucleus accumbens) i.e. the mesolimbic DA system. (J. Pharm. Pharmacol. 25, 1003, 1973).

A number of studies have demonstrated that neuroleptics of different structural classes block the apomorphine stereotypies in the rat and that this blockade is well related to blockade of DA transmission measured by biochemical or neurophysiological techniques. Thus, the antiapomorphine effect correlates well with changes in DA turnover produced by neuroleptic drugs (Eur. J. Pharmacol., 11, 303, 1970), DA receptor binding studies (Life Science, 17, 993-1002, 1976) and most important with antipsychotic efficacy (Nature, 263, 388-341, 1976).

Methods

Male Sprague-Dawley rats (weighing 225-275 g) were used. The rats were observed in perspex cages (40 (L)×25 (w)×30 (h) cm) and the behaviour was scored, 5, 20, 40 and 60 min. after apomorphine. The compounds were injected 60 min. prior to apomorphine hydrochloride (1 mg/kg) which was injected subcutaneously (s.c.) into the neck. This dose and form of administration was found to produce a very consistent response and very low variation in response strength. Further more, apomorphine given s.c. also produced a very consistent hyperactivity.

Directly after injection, the animals were placed in the cages, one in each cage. Scoring of the stereotypies were performed by two separate methods. The first scoring system wa sa modified version of the system introduced by Costall and Naylor (1973). The strength of the stereotype was scored on a 0-3 scale as follows:

| Score | Description of stereotyped behaviour |
|---|---|
| 0 | No change in behaviour compared to saline controls or sedated |
| 1 | Discontinuous sniffing |
| 2 | Continuous sniffing |
| 3 | Continuous sniffing. Chewing. biting and licking. |

In the second system the number of animals displaying hyperactivity caused by apomorphine were scored. Each group consisted of 6-8 animals. Saline controls were always run simultaneously. ED50's are in the first scoring system (0-3 scale), the doses which reduce the strength of the stereotypies by 50% over the observation period of 60 min. ED50's of the second scoring system are the doses which reduce the number of animals showing hyperactivity by 50% over the observation period of 60 min. The ED50 were calculated from log dose-response curves by the method of least squares from 4-6 dose levels with 6-8 animals per dose level.

B. In vitro test: Receptor binding assay

The clinical efficacy of antipsychotic drugs has been shown to correlate with their ability to displace tritiated spiperone from preparations of dopamine receptors (Seeman, Biochem.Pharmacol. 26, 1741 (1977)).

Method

The method of Burt et al. (Proc.Nat. Acad.Sci. USA 72, 4655 (1975) was used. Male Sprague-Dawley rats weighing 150-200 g were decapitated, and their brains were rapidly removed. The striata were dissected, pooled and homogenized in 50 mM Tris-HCl buffer (pH 7.6). The membrane fraction was collected by centrifugation (48000 g for ten minutes), washed once with the buffer, and resuspended in 50 mM Tris-HCl (pH 7.6) containing 0.1% ascrobic acid, 10 mM pargyline, 120 mM NaCl, 5 mM KCl, 2 mM $CaCl_2$ and 1 mM $MgCl_2$. The suspension was preincubated at 37° C. for 10 minutes and then kept on ice until use.

The assays have been carried out using a cell harvester equipment. The incubations were made in quadruplicate, each well containing membrane suspension (2.5 mg/0.5 ml), $^3$H-spiperone (0.4 nM) and the test compound in a final volume of 0.5 ml. After incubation for 10 minutes at 37° C., the contents of the wells were rapidly filtered and washed on Whatman GF/B filters using the Cell harvester. The specific binding was defined as the difference of ligand bound in the presence and in the absence of 1 μM (+)-butaclamol. The test results are expressed as IC50. The IC50 value given in μM, indicates the concentration of the test substance which reduces the amount of specifically bound spiperone by 50%.

Test results

The test results are given in the following table.

TABLE I

| Isomer | Test compound | In vitro Block of $^3$H-spiperone binding IC50 (nM) |
|---|---|---|
| | Prior art compounds: | |
| (S) | 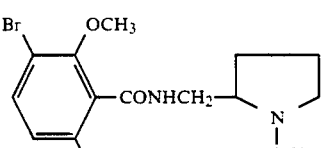<br>(remoxipride U.S. Pat. No. 4 232 037) | 1570 |
| (S) | 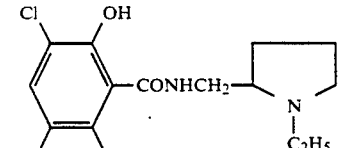<br>(a compound of EP 60235) | 32 |
| | Compounds of the invention: | |
| (S) | 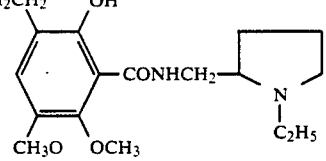 | 2.4 |
| (S) | 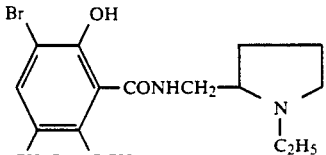 | 1.4 |

TABLE I-continued

| Isomer | Test compound | In vitro Block of $^3$H-spiperone binding IC50 (nM) |
|---|---|---|
| (S) | 3-C$_2$H$_5$, 2-OH, 5-CH$_3$O, 6-OCH$_3$ benzamide –CONHCH$_2$–(N-C$_2$H$_5$ pyrrolidin-2-yl) | 1.3 |
| (S) | 2-OH, 3-CH$_3$O, 6-OCH$_3$ benzamide –CONHCH$_2$–(N-C$_2$H$_5$ pyrrolidin-2-yl) | 8.8 |
| (S) | 3-Cl, 2-OH, 5-CH$_3$O, 6-OCH$_3$ benzamide –CONHCH$_2$–(N-C$_2$H$_5$ pyrrolidin-2-yl) | 0.3 |
| (S) | 3-Br, 2-OH, 5-CH$_3$O, 6-OCH$_3$ benzamide –CONHCH$_2$–(N-CH$_2$CH=CH$_2$ pyrrolidin-2-yl) | 2.3 |
| (R) | 3-Br, 2-OH, 5-CH$_3$O, 6-OCH$_3$ benzamide –CONHCH$_2$–(N-benzyl pyrrolidin-2-yl) | 2.4 |
| (R) | 3-Br, 2-OH, 5-CH$_3$O, 6-OCH$_3$ benzamide –CONHCH$_2$–(N-(4-fluorobenzyl) pyrrolidin-2-yl) | 1.3 |

TABLE II

| | | In vivo | |
|---|---|---|---|
| Isomer | Test compound | Reduction of stereotypies ED50 (μmole/kg i.p.) | Reduction of hyperactivity ED50 (μmole/kg i.p.) |
| | Prior art compounds: | | |
| (S) | 3-Br, 2-OCH$_3$, 6-OCH$_3$ benzamide –CONHCH$_2$–(N-C$_2$H$_5$ pyrrolidin-2-yl) (remoxipride U.S. Pat. No. 4 232 037) | 6.5 | 0.86 |

TABLE II-continued

| | | In vivo | |
|---|---|---|---|
| Isomer | Test compound | Reduction of stereotypies ED50 ($\mu$mole/kg i.p.) | Reduction of hyperactivity ED50 ($\mu$mole/kg i.p.) |
| (S) | 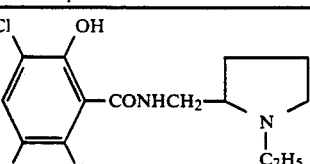 (a compound of EP 60235) | 2.4 | 0.11 |
| | Compounds of the invention: | | |
| (S) | 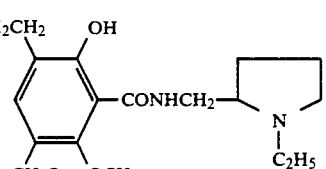 | $26 \cdot 10^{-2}$ | $<10 \cdot 10^{-3}$ |
| (S) | 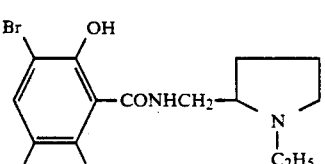 | $4.2 \cdot 10^{-2}$ | $5 \cdot 10^{-3}$ |
| (S) | 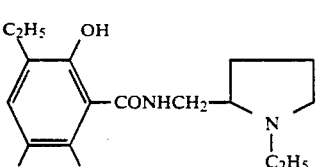 | $5.8 \cdot 10^{-2}$ | $0.7 \cdot 10^{-3}$ |

Comments to the test results

The compounds of this invention exhibit an antidopamine activity superior to that of the tested compounds of the prior art both in vivo and in vitro. In their ability to inhibit the stereotypies induced by apomorphine in rats, the tested compounds of the invention are about 50–150 times more potent than the tested prior art compounds. Moreover, the difference between the ED50 doses which block apomorphine-induced hyperactivity and the ED50 doses which block stereotypies is high, which indicates a highly selective action on specific dopamine neurons. These properties could not be predicted from the properties of the prior art compounds.

The receptor binding studies in vitro confirm the high potency found in vivo of the compounds of the invention. The activity of the compounds of the invention on displacement of $^3$H-spiperone from striatal preparations of the rat brain is very much higher than the activity of the tested prior art compounds.

I claim:

1. A compound of the formula:

$$\text{structure with } R^2, Z^1, Z^2, Z^3 \text{ substituents and } \text{CONHCH}_2\text{-pyrrolidinyl-CH}_2\text{-}R^3$$

or a physiologically acceptable salt or optical isomer thereof, wherein $Z^1$ is OH;
$Z^2$ is $OR^4$;
$Z^3$ is $OCH_3$;
$R^2$ is H, halogen, an alkyl group of 1 to 4 carbon atoms, or $F_3C-(CH_2)_n-$; wherein n is 0, 1 or 2;
$R^3$ is H, an alkyl group of 1 to 4 carbon atoms, an alkenyl group of 2 or 3 carbon atoms, an alkynyl group of 2 or 3 carbon atoms, phenyl, or phenyl substituted with methylene dioxy or one or more fluoro, chloro, bromo, trifluoromethyl, methyl, ethyl, methoxy or ethoxy in the ortho, meta, or para positions; and
$R^4$ is an alkyl group of 1–4 carbon atoms.

2. A compound according to claim 1, selected from the group consisting of:

(S)-(—)-N-[(1-ethyl-2-pyrrolidinyl)methyl]-3-bromo-2-hydroxy-5,6-dimethoxybenzamide;

(S)-(−)-N-[(1-ethyl-2-pyrrolidinyl)methyl]-3-chloro-2-hydroxy-5,6-dimethoxybenzamide;

(S)-(−)-N-[(1-ethyl-2-pyrrolidinyl)methyl]-3-ethyl-2-hydroxy-5,6-dimethoxybenzamide;

(S)-(−)-5,6-dimethoxy-N-[(1-ethyl-2-pyrrolidinyl)methyl]-2-hydroxy-3-propylbenzamide;

(S)-(−)-N-[(1-allyl-2-pyrrolidinyl)methyl]-3-bromo-2-hydroxy-5,6-dimethoxybenzamide;

(R)-(+)-N-[(1-benzyl-2-pyrrolidinyl)methyl]-3-bromo-2-hydroxy-5,6-dimethoxybenzamide;

(S)-(−)-N-[(1-ethyl-2-pyrrolidinyl)methyl]-5,6-dimethoxy-2-hydroxybenzamide hydrochloride; and (S)-(−)-N-[(1-ethyl-2-pyrrolidinyl)methyl]-2-hydroxy-5,6-dimethoxy-3-methylbenzamide.

3. The compound of claim 1 wherein
$Z^1$ is OH;
$Z^2$ is $OCH_3$;
$Z^3$ is $OCH_3$;
$R^2$ is $CH_2CH_2CH_3$; and
$R^3$ is $CH_3$.

4. The compound of claim 1 wherein
$Z^1$ is OH;
$Z^2$ is $OCH_3$;
$Z^3$ is $OCH_3$;
$R^2$ is Br; and
$R^3$ is $CH_3$.

5. The compound of claim 1 wherein
$Z^1$ is OH;
$Z^2$ is $OCH_3$;
$Z^3$ is $OCH_3$;
$R^2$ is $C_2H_5$; and
$R^3$ is $CH_3$.

6. The compound of claim 1 wherein
$Z^1$ is OH;
$Z^2$ is $OCH_3$;
$Z^3$ is $OCH_3$;
$R^2$ is H; and
$R^3$ is $CH_3$.

7. The compound of claim 1 wherein
$Z^1$ is OH;
$Z^2$ is $OCH_3$;
$Z^3$ is $OCH_3$;
$R^2$ is Cl; and
$R^3$ is $CH_3$.

8. The compound of claim 1 wherein
$Z^1$ is OH;
$Z^2$ is $OCH_3$;
$Z^3$ is $OCH_3$;
$R^2$ is Br; and
$R^3$ is $CH=CH_2$.

9. The compound of claim 1 wherein
$Z^1$ is OH;
$Z^2$ is $OCH_3$;
$Z^3$ is $OCH_3$;
$R^2$ is Br; and
$R^3$ is phenyl.

10. The compound of claim 1 wherein
$Z^1$ is OH;
$Z^2$ is $OCH_3$;
$Z^3$ is $OCH_3$;
$R^2$ is Br; and
$R^3$ is para-fluorophenyl.

11. The compound of the formula

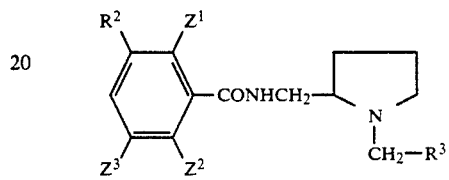

wherein
$Z^1$ is $OCOC_2H_5$;
$Z^2$ is $OCH_3$;
$Z^3$ is $OCH_3$;
$R^2$ is Br; and
$R^3$ is $CH_3$.

12. A pharmaceutical preparation comprising as an active ingredient a compound according to any one of claims 1 or 2-11 or a physiologically acceptable salt or isomer thereof in association with a pharmaceutically acceptable carrier.

13. A method for the treatment of dysfunction of the dopaminergic system in man, comprising administering to a host in need of such treatment an amount of a compound according to any one of claims 1 or 2-11 or a physiologically acceptable salt thereof effective to block dopamine receptors in the brain.

14. The compound of claim 1 wherein:
$Z^1$ is OH;
$Z^2$ is $OCH_3$;
$Z^3$ is $OCH_3$;
$R^2$ is Cl, Br, I, $CH_3$, $CH_2CH_3$ or $CH_2CH_2CH_3$; and
$R^3$ is $CH_3$.

* * * * *

UNITED STATES PATENT AND TRADEMARK OFFICE
CERTIFICATE OF CORRECTION

PATENT NO. : 5,240,957
DATED : August 31, 1993
INVENTOR(S) : Bengtsson et al.

It is certified that error appears in the above-indentified patent and that said Letters Patent is hereby corrected as shown below:

Col. 1, lines 20-21, change "psychomatic" to -- psychosomatic--;

Col. 2, line 31, change "sates" to --states--;

Col. 2, line 33, change "chloride" to --chlorine--;

Col. 5, line 3, after "citrate," insert --,--;

Col. 5, line 58, after "ethanol," insert --,--;

Col. 7, line 31, change "diphosphoruspentoide" to --diphosphoruspentoxide--;

Col. 7, line 35, change "diccylohexylcarbodiimide" to --dicyclohexylcarbodiimide--;

Col. 8, line 18, after "$NH_2$," insert --$NR^4$,--;

Col. 8, line 56, change "hydroxyl," to --hydroxy--;

Col. 9, line 24, change "iodtrimethylsilane" to --iodotrimethylsilane--;

Col. 9, line 55, change "chloromaides" to --chloroamides--;

Col. 9, line 64, change "catalysts" to --catalysis--;

Col. 10, line 52, change "staring" to --starting--;

Col. 11, line 20, delete "or $OR^4$;"

UNITED STATES PATENT AND TRADEMARK OFFICE
CERTIFICATE OF CORRECTION

PATENT NO. : 5,240,957
DATED : August 31, 1993
INVENTOR(S) : Bengtsson et al.

It is certified that error appears in the above-indentified patent and that said Letters Patent is hereby corrected as shown below:

Col. 11, line 43, change "I" to --II--;

Col. 12, line 10, change "intermediate" to --intermediates--;

Col. 13, line 10, delete "N-[( "

Col. 13, line 11, after "ethyl," delete "- "

Col. 13, line 17, change "NRM" to --NMR--;

Col. 13, line 22, change "calc." to --calcd--;

Col. 13, line 46, change "steps" to --stops--;

Col. 13, line 49, change "mixture" to --mixtured--;

Col. 13, line 57, change "Recrylstallization" to --Recrystallization--;

Col. 14, line 42, change "(Sx2, 6H)" to --(sx2, 6H)--;

Col. 14, line 47, change "mol" to --mmol--;

Col. 14, line 61, change "(+)" to --(-)--;

Col. 15, line 34, delete "N- "

Col. 16, line 2, after "5.67," insert --;--;

Col. 16, line 3, change "8.36" to --8.37--;

Col. 16, line 19, delete "(-)-;"

UNITED STATES PATENT AND TRADEMARK OFFICE
CERTIFICATE OF CORRECTION

PATENT NO. : 5,240,957
DATED : August 31, 1993
INVENTOR(S) : Bengtsson et al.

It is certified that error appears in the above-indentified patent and that said Letters Patent is hereby corrected as shown below:

Col. 16, line 29, after "hydroxy," insert -- - --;

Col. 16, lines 33 and 67 and Col. 18, line 11, change "trimethoxyhydroxybenzamide" to --trimethoxybenzamide--;

Col. 17, line 5, change "(54))" to --(54%)--;

Col. 17, line 34, change "0.27" to --0.027--;

Col. 18, line 15, after " (S, OCH$_3$)" insert --3.83 (s, OCH$_3$),--;

Col. 18, line 25, change "5.30" to --5.20--;

Col. 18, line 67, after "(-)", insert --3-bromo- --;

Col. 20, line 27, change "cacld" to --calcd--;

Col. 20, line 44, change "trimethoxybenzamide" to --trimethoxybenzoyl--;

Col. 20, line 53, delete "-(+)";

Col. 20, line 57, after "N- " insert --(--;

Col. 21, line 4, after the first "1H " insert --)--;

UNITED STATES PATENT AND TRADEMARK OFFICE
CERTIFICATE OF CORRECTION

PATENT NO. : 5,240,957
DATED : August 31, 1993
INVENTOR(S) : Bengtsson et al.

It is certified that error appears in the above-indentified patent and that said Letters Patent is hereby corrected as shown below:

Col. 21, line 7, change "1458:8" to --145.8--;

Col. 21, line 15, delete "(-)-;"

Col. 21, line 21, after "95," insert --%--;

Col. 21, line 47, change "methoxybenzamide" to --methoxybenzoic--;

Col. 21, line 65, after "7.38," change ")" to --(--;

Col. 22, lines 3, 5, 17 and 20, delete "N-;"

Col. 22, line 26, after "1," insert --H--;

Col. 22, line 27, delete --ppm--;

Col. 22, line 45, change "2-hydroxy-6-methoxybenzamide" to --5,6-diethoxy-2-hydroxybenzamide--;

Col. 24, line 53, change "wa sa" to --was a--.

Signed and Sealed this

Tenth Day of March, 1998

*Attest:*

*Attesting Officer*

BRUCE LEHMAN
*Commissioner of Patents and Trademarks*